(12) United States Patent
Hiiro

(10) Patent No.: US 7,436,517 B2
(45) Date of Patent: Oct. 14, 2008

(54) OPTICAL MEASURING APPARATUS

(75) Inventor: Hiroyuki Hiiro, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 106 days.

(21) Appl. No.: 11/392,588

(22) Filed: Mar. 30, 2006

(65) Prior Publication Data

US 2006/0221345 A1 Oct. 5, 2006

(30) Foreign Application Priority Data

Mar. 30, 2005 (JP) ............... 2005-098334

(51) Int. Cl.
*G01B 9/02* (2006.01)
*G01J 3/45* (2006.01)
(52) U.S. Cl. ...................... 356/451; 356/479
(58) Field of Classification Search .......... 356/311, 356/317, 451, 477, 479; 250/227.19, 227.27; 372/6
See application file for complete search history.

(56) References Cited

U.S. PATENT DOCUMENTS 6,744,960 B2 * 6/2004 Pelka ........................ 385/130

2004/0239942 A1 * 12/2004 Sun ............................ 356/479

OTHER PUBLICATIONS

Adolf F. Fercher, "Optical Coherence Tomography", Journal of Biomedical Optics, vol. 1, No. 2, pp. 157-173, 1996.
Hao Zhang, et al., "From Water-Soluble CdTe Nanocrystals to Fluorescent Nanocrystal-Polymer Transparent Composites Using Polymerizable Surfactants", Advanced Materials, vol. 15, No. 10, pp. 777-780, 2003.
Melissa A. Petruska, et al., "High-Performance, Quantum Dot Nanocomposites for Nonlinear Optical and Optical Gain Applications", Advanced Materials, vol. 15, No. 7-8, pp. 610-613, 2003.

* cited by examiner

*Primary Examiner*—Michael A Lyons
(74) *Attorney, Agent, or Firm*—Sughrue Mion, PLLC

(57) ABSTRACT

Excitation light is inputted to an optical element with uniformly dispersed inorganic fluorescent nanoparticles whose radius is controlled. Fluorescence is emitted from the inorganic fluorescent nanoparticles through photoexcitation and outputted from one end of the optical element. By controlling the radius of the inorganic fluorescent nanoparticles dispersed in the optical element, the wavelength range and spectral width of the light outputted from the optical element are controlled.

11 Claims, 2 Drawing Sheets

OPTICAL MEASURING APPARATUS

BACKGROUND OF THE INVENTION

1. Field of the Invention

The present invention relates to an optical measuring apparatus for measuring characteristics of a test section using light emitted from a light source.

2. Description of the Related Art

Various types of optical measuring systems for measuring characteristic of a test section using light emitted from a light source are known. Optical measurement allows nondestructive testing of semiconductors, disks, living bodies, and the like. For example, optical coherence tomography systems (OCT systems) for obtaining an optical tomographic image of a test section of a living body or the like have already been put into practical use in the medical field or the like. In such systems, the optical tomographic image is obtained by irradiating light on the test section and using the light reflected from or transmitted through the test section.

Various types of OCT systems have been developed. An OTDR (optical time domain reflectometry) that uses an SLD (super-luminescent diode) as the light source is used in eye clinics or the like. In the OTDR described above, low coherence light emitted from the SLD light source is branched into measuring light and reference light by a beam splitter. The reference light is inputted to a reference light mirror which is periodically driven by a PZT and the measuring light is irradiated on the test object. The reference light reflected from the reference light mirror and the measuring light incident on the test object and reflected from a predetermined depth of the test object are combined by the beam splitter and inputted to a single mode fiber. That is, the optical path is formed by a Michelson interferometer. Here, if the optical path length of the reference light and that of the measuring light correspond with each other within the range of the coherence length of the low coherence light, the interference between the reference light and measuring light is observed, and if they do not, the interference is not observed.

Interference fringes may be observed through heterodyne detection of the envelopes of the fringes using a photo diode. The position of the test object relative to the reference light mirror may be measured by periodically scanning the positions in the optical axis direction of the reference light mirror. The tomographic image of the test object may be obtained by periodically scanning the positions in the optical axis direction of the reference light mirror and scanning the test object in the direction orthogonal to the optical axis simultaneously.

The OTDR described above requires a mechanical scanning in the optical axis direction. Recently, however, development work is proceeding with an OFDR (optical frequency domain reflectometry), which is an OCT system that does not require scanning in the optical axis direction. The OFDR also comes in variety of types. For example, an OFDR using broadband spectral interferometry may obtain a tomographic image of test section by detecting interference light from the interferometer as a channeled spectrum in which the interference light is optically broken up into each wavenumber component and analyzing it through Fourier analysis without performing the scanning in the depth direction as described, for example, in the document entitled "Optical Coherence Tomography" by A. F. Fercher, Journal of Biomedical Optics, Vol. 1, No. 2, pp. 157-173, 1996.

When measuring characteristics of the interior structure of the test section or the like, it is preferable to use light with a wavelength that matches with the light transmission characteristics of the test section, that is, the wavelength having a highest optical transmittance for the test section. Further, it is preferable that different optical measuring methods use light with different wavelengths appropriate for the respective methods.

In the conventional light source that uses a laser, an SLD or the like, however, it is difficult to set the oscillation wavelength arbitrarily because the wavelength of the light emitted from the light source is determined by the composition of the gain medium. Thus, the optical measuring system using such light source has a problem that it is unable to perform measurement using light with an appropriate wavelength according to the optical transmittance, measuring method employed, or the like.

The present invention has been developed in view of the circumstances described above, and it is an object of the present invention to provide an optical measuring apparatus that allows measurement using light with an appropriate emission wavelength according to the optical transmittance of a test section, measuring method employed, or the like.

SUMMARY OF THE INVENTION

The optical measuring apparatus of the present invention is a measuring apparatus for measuring characteristics of a test section using light emitted from a light source, wherein the light source comprises:

an optical element with multitudes of inorganic fluorescent nanoparticles dispersed therein, the fluorescence energy level of the nanoparticles being controllable by the diameter thereof; and an excitation light source for emitting excitation light with a wavelength in the wavelength range capable of photoexciting the fluorescence energy level of the inorganic fluorescent nanopaticles.

The referent of "nanoparticle" as used herein means a particle with a diameter not greater than 20 nm. As for the inorganic fluorescent nanopaticles, particles of the same material with the same diameter, composite particles constituting a plurality of different groups, each made of the same material with different diameters, composite particles constituting a plurality of different groups, each made of different materials with the same diameter, or composite particles constituting a plurality of different groups, each made of different materials with different diameters may be used. When particles of the same material with the same diameter are used, monochromatic light is emitted from the light source. When composite particles constituting a plurality of different groups are used, heterochromatic light is emitted from the light source. Further, when composite particles constituting a plurality of different groups in which the diameter of the particles is varied almost continuously from group to group, broadband light is emitted from the light source.

If the optical element includes a plurality of inorganic fluorescent nanoparticles having different fluorescence energy levels dispersed therein, the emission spectral width (full width at half maximum) of the light emitted from the light source may be greater than or equal to 100 nm.

The optical element may be an optical waveguide. Further, the optical waveguide may be an optical fiber having a core made of a polymer or glass material.

The optical measuring apparatus of the present invention may further comprise:

an branching/combining means for branching the light emitted from the light source into measuring light and reference light, irradiating the measuring light on a test section, and interfering reflected light of the measuring light reflected from a predetermined depth of the test section with the reference light;

a measuring means for measuring the light intensity of the interference light produced by the reflected light and reference light; and an image generating means for obtaining an optical tomographic image of the test section based on the light intensity of the interference light obtained by the measuring means.

The light source described above includes an optical element with multitudes of inorganic fluorescent nanoparticles dispersed therein, the fluorescence energy level of the nanoparticles being controllable by the diameter thereof, and an excitation light source for emitting excitation light with a wavelength in the wavelength range capable of photoexciting the fluorescence energy level of the inorganic fluorescent nanopaticles. Consequently, an optical measuring apparatus that allows measurement using light with an intended wavelength may be realized by exciting the inorganic fluorescent nanoparticles dispersed in the optical element to generate fluorescence with the intended wavelength and outputting the fluorescence from one end of the optical element.

As for the material of the inorganic fluorescent nanoparticles, an appropriate semiconductor or dielectric material, or the like having a bulk band gap energy which is smaller (longer wavelength) than that of an intended wavelength may be used. The energy level of the inorganic fluorescent nanoparticle is determined mostly by the particle diameter due to its unique quantum confinement effect, and a smaller particle diameter results in a larger energy level.

The following formula approximates the lowest exciton energy Eex of an inorganic fluorescent nanoparticle with a radius of R.

$$Eex = \left[ Eg^2 + 2\hbar^2 Eg \frac{(\pi|R)^2}{\mu} \right]^{1/2} \quad (1)$$

where:
Eg: band gap energy of bulk crystal (eV)
R: radius of nanoparticle (nm)
μ: effective mass
$\hbar$: Planck's constant=6.58×10$^{-16}$ (eV·s)

Accordingly, the wavelength of the fluorescence emitted from the inorganic fluorescent nanoparticle may be approximated by the following formula (formula 2) based on the energy obtained by the formula (1) above.

$$\lambda \approx 1240/Eex \text{(nm)} \quad (2)$$

As the formula (1) indicates, the lowest energy of the inorganic fluorescent nanoparticle is higher than the band gap energy of the bulk crystal, and the smaller the particle diameter, the higher the energy.

Based on the formulae (1) and (2), the particle diameter of the inorganic nonpariticle required for obtaining fluorescence with an intended wavelength may be determined. Accordingly, by controlling the particle diameter of the inorganic nonoparticles, the fluorescent energy level may be shifted to the level that corresponds to an intended wavelength which is on the higher energy side than the bulk energy gap.

In the mean time, it is often the case that an SLD is used as the broadband low coherence light source for an OCT system and the like. The SLD may be substituted by a semiconductor laser so that it has a high versatility as a small, simple, and inexpensive light source. But the optical spectral width is determined mostly by the gain width of the gain medium of the semiconductor laser. Thus, the optical spectral width is limited to around 30 to 40 nm that corresponds to the gain width of an ordinary semiconductor laser.

In the mean time, the coherence length Lc of a light source is inversely proportional to the optical spectral width of the light source, and may be expressed by the following formula (formula 3).

$$Lc \approx \frac{c}{\Delta\omega} \quad (3)$$

where:
Δω: spetral width of the light source
c: speed of light

The formula indicates that the resolution of an optical tomographic image in the depth direction is determined mostly by the optical spectral width of the light source. That is, a greater optical spectral width of the light source allows measurement with higher resolution.

Where further high image resolution is required in the depth direction, a low coherence light source with a greater emission spectral width (broadband) is required. If an SLD is used as the light source, however, the optical spectral width is determined by the gain width of the semiconductor laser as described above. Therefore, the image resolution in the depth direction is limited by this. Accordingly, in the system that requires further high image resolution in the depth direction has a problem with the SLD light source that uses a semiconductor laser in that it can not provide a sufficient emission spectral width for such applications.

In the mean time, an OCT system that employs a mode lock titanium sapphire laser as the light source capable of emitting broadband low coherence light to obtain image resolution in the depth direction as high as several micrometers is reported. The mode lock titanium sapphire laser, however, is not suited for practical use since it is expensive and difficult to handle as the light source.

The optical measuring apparatus of the present invention includes an optical element with a plurality of inorganic fluorescent nanoparticles having different fluorescence energy levels dispersed therein as the light source to provide light with an optical spectral width (full width at half maximum) of greater than or equal to 100 nm. In this way, the present invention may realize an optical measuring apparatus which is inexpensive and easy to handle.

That is, for the light source that includes an optical element with a plurality of inorganic fluorescent nanoparticles having different fluorescence energy levels dispersed therein, an intended fluorescence spectral width may be obtained by dispersing the nanoparticles such that the particle diameters are distributed in an intended fashion. Neither the emission spectral width nor the emission range is limited by the gain width as in the semiconductor laser. Accordingly, light with almost any emission spectral width in almost any emission range may be provided by the light source. Here, the material of the nanoparticles is not limited to a single material, and nanoparticles made of two or more different materials may be mixed together as required.

When an optical waveguide is used as the optical element described above, a simple light source may be produced. Further, if an optical fiber having a core made of a polymer or glass material is used as the optical waveguide, a long optical waveguide may be produced easily and thereby high intensity light may be outputted from the light source.

When the optical measuring apparatus of the present invention includes a branching/combining means for branching the light emitted from the light source into measuring light and reference light, irradiating the measuring light on a test section, and interfering reflected light of the measuring light reflected from a predetermined depth of the test section with the reference light; a measuring means for measuring the light intensity of the interference light produced by the reflected light and reference light; and an image generating means for obtaining an optical tomographic image of the test section based on the light intensity of the interference light obtained by the measuring means, an optical tomographic image may be obtained by the apparatus which is inexpensive and easy to handle.

Further the light source that includes an optical element with a plurality of inorganic fluorescent nanoparticles having different fluorescence energy levels dispersed therein may realize an optical spectral width of greater than or equal to 100 nm easily.

DESCRIPTION OF THE PREFERRED EMBODIMENTS

Figure 1:
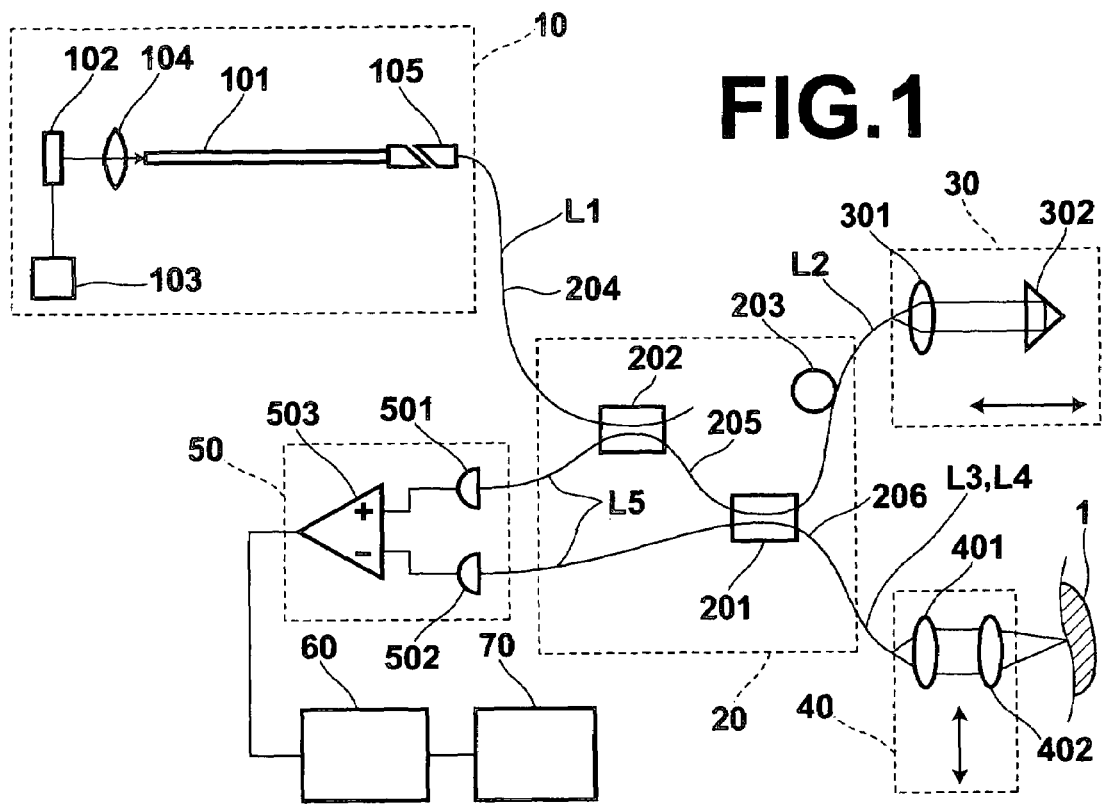
FIG. 1 is a schematic configuration diagram of the optical tomography imaging apparatus according to an embodiment of the present invention illustrating the configuration thereof.

Hereinafter, an optical tomography imaging apparatus which is a first specific embodiment of the present invention will be described with reference to accompanying drawings. FIG. 1 is a schematic configuration diagram of the optical tomography imaging apparatus of the present invention. The optical tomography imaging apparatus of the present embodiment is an apparatus for obtaining an optical tomographic image of a test section 1, which is living tissue.

The optical tomography imaging apparatus of the present embodiment includes a light source section 10 for providing broadband low coherence light L1 with a spectral width of 200 nm in the emission range of 1000 nm to 1200 nm; a fiber coupling optical system 20 for branching the low coherence light L1 emitted from the light source section 10 into reference light L2 and measuring light L3, and combining them; an optical path delaying section 30 placed in the optical path of the reference light L2 for changing the optical path length thereof; an optical scanning section 40 for scanning the test section 1, which is living tissue covered with a substance 2 that includes water, with the measuring light L3. The apparatus further includes a balanced difference detecting section 50 for detecting the intensity of interference light L5 produced by reflected light 4 reflected from a predetermined depth of the test section 1 and the reference light L2; a signal processing section 60 for converting the reflected light L4 reflected from a predetermined depth of the test section 1 to an image signal by performing heterodyne detection to obtain the intensity of the reflected light L4 based on the intensity of the interference light L5 detected by the balanced difference detecting section 50; and an image displaying section 70 for displaying the image signal obtained by the signal processing section 60 as a tomographic image.

The light source section 10 includes an optical fiber 101 having a core with inorganic fluorescent nanoparticle groups uniformly dispersed therein in which diameters of the nanoparticles are varied continuously from group to group so that the lowest exciton energy is distributed uniformly in the range of 1000 nm to 1200 nm which is best suited for measuring living bodies or the like; a semiconductor laser 102 for emitting excitation light with a wavelength of 950 nm; a power source 103 for driving the semiconductor laser 102; a lens 104 for inputting the excitation light emitted from the semiconductor laser 102 to the optical fiber 101; and an optical connector 105 for guiding and inputting the broadband coherence light L1 outputted from the optical fiber 101 to the fiber coupling optical system 20 in the subsequent stage.

Preferably, the wavelength of the excitation light for exciting the inorganic fluorescent nanoparticle groups is shorter than those of the fluorescence emitted from the nanoparticle groups.

As for the material of the inorganic fluorescent nanoparticles dispersed in the optical fiber 101, any material may be used as long as it has a band gap energy which is slightly smaller than that corresponding to the wavelength of 1200 nm. Thus, semiconductor crystals, such as iron sulfide ($FeS_2$), iron silicide ($\beta$-$FeSi_2$), lead sulfide (PbS), germanium (Ge), and the like may be used. Quality nanocrystals of iron sulfide and lead sulfide are realized by the hot soap method. Nanocrystals of iron silicide may be formed by the vacuum electron beam evaporation or the like. Further, Nanocrystals of germanium may be formed by the supercritical fluid technique. In particular, nanocrystals formed by chemical methods including the hot soap method have very high conversion efficiency from the excitation light to the fluorescence, and conversion efficiency of several to several tens of percent may be achieved. In the present embodiment, lead sulfide is used as the material of inorganic fluorescent nanoparticles.

As for the core material in which such nanoparticles are dispersed, a polymer or glass may be used. The method for dispersing nanoparticles in a polymer is described, for example, in the document entitled "From Water-Soluble CdTe Nanocrystals to Fluorescent Nanocrystal-Polymer Transparent Composites Using Polymerizable Surfactants" by H. Zhang et al., Advanced Materials, Vol. 15, No. 10, pp. 777-780, 2003. The method for dispersing nanoparticles in glass is described, for example, in the document entitled "High-Performance, Quantum Dot Nanocomposites for Nonlinear Optical and Optical Gain Applications" by M. A. Petruska et al., Advanced Materials, Vol. 15, No. 7-8, pp. 610-613, 2003.

The following values for the band gap energy Eg and effective mass μ of the bulk crystal in the inorganic fluorescent nanoparticles of lead sulfide are substituted in the formulae (1) and (2) above.

Eg: band gap energy of bulk crystal=0.41 (eV)

μ: effective mass$\approx 0.085 \times m_e = 0.085 \times 9.1093826 \times 10^{-31}$ (Kg)

Figure 2:
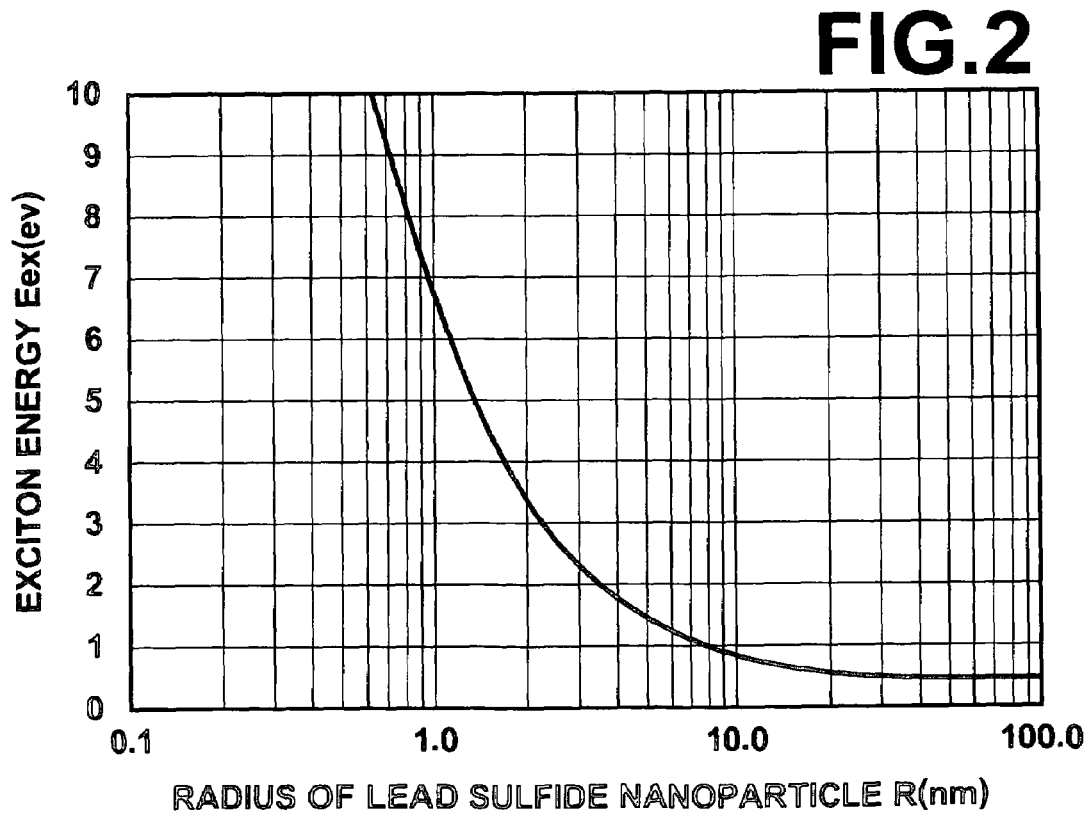
FIG. 2 is a graph illustrating the relationship between the radius of nanoparticle and exciton energy thereof.
Figure 3:
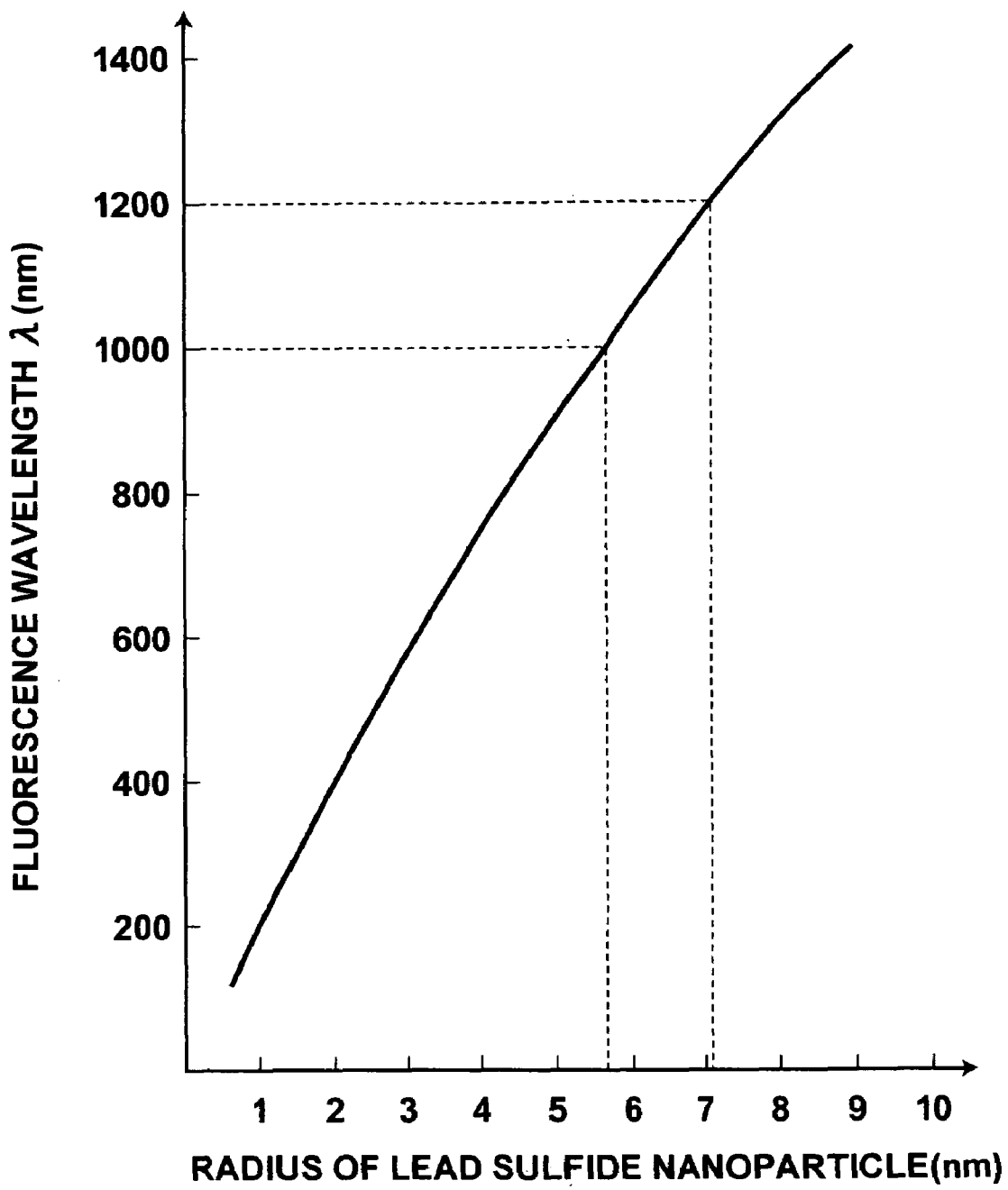
FIG. 3 is a graph illustrating the relationship between the radius of nanoparticle and wavelength of the fluorescence emitted therefrom.

FIG. 2 is a graph illustrating the relationship between the radius R of the nanoparticle in formula (1) and the lowest exciton energy Eex thereof. FIG. 3 is a graph illustrating the relationship between the radius R of the nanoparticle in formula (2) and the wavelength of the fluorescence emitted therefrom.

FIG. 3 shows that the wavelength of the fluorescence emitted from the lead sulfide nanoparticle is 1000 nm when the radius thereof is 5.75 nm. The wavelength becomes longer as the radius becomes greater and it becomes 1200 nm when the radius thereof is 7.1 nm. This means that broadband coherence light in the wavelength range of approximately 1000 nm to 1200 nm may be obtained by controlling the radius R of the lead sulfide nanoparticles in the range of 5.75 to 7.1 nm.

The lead sulfide nanoparticles are dispersed transparently and uniformly in a polymer. Consequently, the fluorescence with wavelengths corresponding to the energies determined by the particle diameters emitted from the nanoparticles excited by the excitation light propagates within the core of the optical fiber toward the output end of the fiber. By outputting the fluorescence from one end of the optical fiber, low coherence light with an intended emission spectral width in an intended wavelength range may be obtained.

When the optical fiber is constructed to allow only single transverse mode light to be propagated, the output light from the optical fiber becomes a point light source. Uniform dispersion of inorganic nanoparticles in a polymer or glass material with the transparency being maintained may be implemented by coordinating ligands having compatibility with the polymer or glass material on the surface of the inorganic nanoparticles.

Further, in the present embodiment, an end face inputting type light source in which the excitation light is inputted from the end face of the optical fiber is described. But a lateral face inputting type light source in which the excitation light is inputted from the lateral face of the optical fiber may also be used.

The fiber coupling optical system 20 includes a fiber coupler 202 for branching the low coherence light L1 outputted from the light source section 10 into the measuring light L3 and reference light L2, and combining the reflected light L4 of the measuring light L3 reflected from a predetermined depth of the test section 1 and reference light L2 to obtain the interference light L5; a fiber coupler 202 provided between the light source section 10 and fiber coupler 201; a piezo element 203 for causing a slight frequency shift in the reference light L2; a fiber 204 for linking the light source 10 to the fiber coupler 202; a fiber 205 for linking the optical path delaying section 30 to the balanced difference detecting section 50 through the fiber couplers 201 and 202; and a fiber 206 for linking the optical scanning section 40 to the balanced difference detecting section 50. The fibers 204, 205 and 206 are single mode optical fibers.

The optical path delaying section 30 includes a lens 301 for converting the reference light L2 outputted from the fiber 205 to collimated light and inputting the reflected reference light L2 to the fiber 205; and a prism 302 for changing the optical path length of the reference light L2 by horizontal movements in FIG. 1.

The scanning section 40 includes lenses 401 and 402 for moving the measuring light L3 in vertical directions in FIG. 1, and inputting the reflected light L4 reflected from the test section 1 to the fiber 206.

The balanced difference detecting section 50 includes photodetectors 501 and 502 for measuring the intensity of the interference light L5; and a differential amplifier 503 for amplifying the difference between the values detected by the photodetectors 501 and 502 after the input balance between the photodetectors 501 and 502 is adjusted to cancel out the noise and drift components. The photodetectors 501 and 502 are InGaAs photodetectors having detection sensitivity for the light with a wavelength greater than or equal to 0.98 μm.

Hereinafter, the operation of the optical tomography imaging system according to the present embodiment will be described. Initially, the excitation light with a wavelength of 950 nm emitted from the semiconductor laser 102 is inputted to the core of the optical fiber 101. This causes the lead sulfide nanoparticle groups included in the core of the optical fiber 101 to be photoexcited, and fluorescence with wavelengths from 1000 to 1200 nm is emitted from the nanoparticles. The fluorescence emitted from the nanoparticles is outputted from one end of the optical fiber 101 and inputted to the fiber 204 of the fiber coupling optical system 20 through the optical connector 105, which means that broadband low coherence light L1 is outputted from the light source section 10.

The broadband low coherence light L1 transmitted through the fiber 204 is introduced to the fiber 205 through the fiber coupler 202, and branched by the fiber coupler 201 into the reference light L2 propagating through the fiber 205 toward the optical path delaying section 30 and the measuring light L3 propagating through the fiber 206 toward the optical scanning section 40.

The reference light L2 is modulated by the piezo element 203 provided in the optical path thereof to cause a slight frequency difference Δf between the reference light L2 and measuring light L3.

The measuring light L3 is incident on the test section 1 through the lenses 401 and 402 of the optical scanning section 40. The reflected light L4 which is a part of the measuring light L3 incident on the test section 1 and reflected from a predetermined depth thereof is returned to the fiber 206. The reflected light L4 returned to the fiber 206 is combined with the reference light L2 returned to the fiber 205 to be described later at the fiber coupler 201.

In the mean time, the reference light L2 modulated by the piezo element 203 transmits through the fiber 205 and is incident on the prism 302 through the lens 301, which is reflected from the prism 302 and returned to the fiber 205 again through the lens 301. The reference light L2 returned to the fiber 205 is combined with the reflected light L4 described above at the fiber coupler 201.

The reflected light L4 and reference light L2 combined by the fiber coupler 201 coaxially overlap with each other, and interfere with each other under a predetermined condition to produce a beam signal as the interference light L5.

The reference light L2 and reflected light L4 interfere with each other when the optical path length of the measuring light L3 (reflected light L4) for reaching the fiber coupler 201 is substantially equal to the optical path length of the reference light L2 for reaching the fiber coupler 201 after the low coherence light L1 is branched into the measuring light L3 and reference light L2, since both the reference light L2 and reflected light L4 are the low coherence light L1 with a short coherence length. Consequently, a beat signal beating at the frequency difference (Δf) between the two interfering light waves is produced.

The interference light L5 is branched into two by the fiber coupler 201, and one of which is inputted to the photodetector 501 of the balanced difference detecting section 50 through the fiber 205, and the other is inputted to the photodetector 502 through the fiber 206.

The light intensity of the beat signal is detected by the photodetectors 501 and 502 based on the interference light L5, and the difference between the values detected by the photodetectors 501 and 502 is obtained by the differential amplifier 503 and outputted to the signal processing section 60. The differential amplifier 503 has a capability to adjust the balance of DC component of the input values. Consequently, even if the low coherence light L1 emitted from the light source section 10 should be drifting, the drift component may be offset by first adjusting the balance of the DC component, and then amplifying the difference. Thereby only the beat signal component may be detected. Further, a part of the low coherence light L1 emitted from the light source section 10 is superimposed on the interference light L5 to be inputted to the photodetector 501, so that the drift component may be offset at the differential amplifier 503.

Further, if the prism 302 is moved in the optical axis directions (horizontal directions in FIG. 1), the optical path length of the reference light L2 for reaching the fiber coupler 201 is changed. Consequently, the optical path length of the measuring light L3 (reflected light L4) that interferes with the reference light L2 is also changed. That is, the depth of the test section 1 for obtaining the tomographic information is varied.

After obtaining the tomographic information at a predetermined point of the test section 1 from the surface to an intended depth in the manner as described above, the incident point of the measuring light L3 is moved slightly by the lenses 401 and 402 of the optical scanning section 40 in the vertical direction in FIG. 1 to obtain the tomographic information of the test section 1 at that point from the surface to a predetermined depth in the same manner as described above. By repeating such operation, the tomographic image of the test section 1 may be obtained.

The signal processing section 60 performs heterodyne detection for obtaining the intensity of the reflected light L4 reflected from a predetermined depth of the test section 1 based on the intensity of the interference light L5 detected by the balanced difference detecting section 50, which is converted to an image signal and displayed on the image displaying section 70 as a tomographic image.

As described above, the optical tomography imaging apparatus of the present invention employs the light source section 10 as the light source capable of emitting the broadband low coherence light L1 in the wavelength range of approximately 1000 nm to 1200 nm which is suitable for obtaining an optical tomographic image of living tissue. The light source section 10 includes the optical fiber having the core with lead sulfide nanoparticle groups uniformly dispersed therein whose radius R is controlled from 5.75 nm to 7.1 nm, and the broadband low coherence light L1 is obtained by exciting the optical fiber using the excitation light with a wavelength of 950 nm. Consequently, an optical tomography imaging apparatus which is inexpensive and easy to handle may be realized.

Further, the light source 10 includes the optical fiber 101 with a plurality of inorganic fluorescent nanoparticles having different fluorescence energy levels dispersed therein, an optical spectral width of 200 nm may be realized easily. The optical tomography apparatus of the present invention employing such light source 10 may realize high image resolution inexpensively.

Still further, the optical fiber 101 with the core made of a polymer material is used, so that a long optical waveguide which may withstand damages may be formed, and thereby high intensity light may be outputted from the light source 10.

In the present embodiment, the light source 10 is applied to the OTDR type OCT system. But the application of the light source 10 is not limited to this, and it may be used for the OFDR type OCT system and other optical measuring systems. Further, it is preferable that the wavelength range and spectral width of the light emitted from the light source 10 are preset to optimal values according to the optical measuring system to which the light source 10 is applied or the type of the test section by controlling the radius R of the inorganic fluorescent nanoparticles dispersed in the optical fiber 101.

What is claimed is:

1. An optical measuring apparatus for measuring characteristics of a test section using light emitted from a light source, wherein the apparatus comprises:
   an optical element with multitudes of inorganic fluorescent nanoparticles dispersed therein, the fluorescence energy level of the nanoparticles being controllable by the diameter thereof;
   an excitation light source for emitting excitation light with a wavelength in the wavelength range capable of photo-exciting the fluorescence energy level of the inorganic fluorescent nanoparticles;
   a branching/combining means for branching the light emitted from the light source into measuring light and reference light, irradiating the measuring light on a test section, and interfering reflected light of the measuring light reflected from a predetermined depth of the test section with the reference light;
   a measuring means for measuring the light intensity of the interference light produced by the reflected light and reference light; and
   an image generating means for obtaining an optical tomographic image of the test section based on the light intensity of the interference light obtained by the measuring means.

2. The optical measuring apparatus according to claim 1, wherein the optical element includes a plurality of inorganic fluorescent nanoparticles having different fluorescence energy levels dispersed therein; and
   the emission spectral width (full width at half maximum) of the light emitted from the light source is greater than or equal to 100 nm.

3. The optical measuring apparatus according to claim 2, wherein the optical element is an optical waveguide.

4. The optical measuring apparatus according to claim 3, wherein the optical waveguide is an optical fiber having a core made of a polymer or glass material.

5. The optical measuring apparatus according to claim 1, wherein the optical element is an optical waveguide.

6. The optical measuring apparatus according to claim 5, wherein the optical waveguide is an optical fiber having a core made of a polymer or glass material.

7. The optical measuring apparatus according to claim 6, wherein the optical waveguide is a single-mode fiber.

8. The optical measuring apparatus according to claim 1, wherein the light source provides light with a spectral width of 200 nm in the emission range of 1000 nm to 1200 nm.

9. The optical measuring apparatus according to claim 8, wherein the light source comprises inorganic fluorescent nanoparticle groups uniformly dispersed therein;
   wherein diameters of the nanoparticles are varied continuously from group to group so that the lowest exciton energy is distributed uniformly in the range of 1000 nm to 1200 nm.

10. The optical measuring apparatus according to claim 1, wherein the nanoparticles comprise lead sulfide.

11. The optical measuring apparatus according to claim 10, wherein the nanoparticles are of radiuses from about 5.75 nm to about 7.1 nm.

* * * * *